United States Patent [19]
Haffner et al.

[11] Patent Number: 6,045,900
[45] Date of Patent: Apr. 4, 2000

[54] BREATHABLE FILLED FILM LAMINATE

[75] Inventors: William Bela Haffner, Kennesaw; Ann Louise McCormack, Cumming, both of Ga.

[73] Assignee: Kimberly-Clark Worldwide, Inc., Neenah, Wis.

[21] Appl. No.: 08/929,562

[22] Filed: Sep. 15, 1997

[51] Int. Cl.⁷ ........................................ B32B 5/18
[52] U.S. Cl. ........................... 428/315.9; 428/315.9; 428/316.6; 428/317.9; 428/332; 442/370; 442/394; 442/398
[58] Field of Search .................. 442/394, 398; 428/315.5, 315.9, 317.9, 316.6, 332

[56] References Cited

U.S. PATENT DOCUMENTS

| | | | |
|---|---|---|---|
| 3,645,992 | 2/1972 | Elston | 260/80.78 |
| 3,894,904 | 7/1975 | Cook | 156/229 |
| 4,147,827 | 4/1979 | Breit, Jr. et al. | 428/218 |
| 4,154,885 | 5/1979 | Tecl et al. | 428/198 |
| 4,190,624 | 2/1980 | Alard et al. | 264/146 |
| 4,194,041 | 3/1980 | Gore et al. | 428/315 |
| 4,197,150 | 4/1980 | Breidt, Jr. et al. | 156/229 |
| 4,252,851 | 2/1981 | Lansbury et al. | 428/336 |
| 4,265,954 | 5/1981 | Romanek | 428/85 |
| 4,276,330 | 6/1981 | Stanley | 428/35 |
| 4,289,832 | 9/1981 | Schwarz | 428/542 |
| 4,297,408 | 10/1981 | Stead et al. | 428/240 |
| 4,303,708 | 12/1981 | Gebhardt et al. | 428/35 |
| 4,306,559 | 12/1981 | Nishizawa et al. | 128/287 |
| 4,312,964 | 1/1982 | Sekine et al. | 525/88 |
| 4,341,216 | 7/1982 | Obenour | 128/287 |
| 4,343,848 | 8/1982 | Leonard, Jr. | 428/156 |
| 4,344,999 | 8/1982 | Gohlke | 428/212 |
| 4,347,408 | 9/1982 | Ohki et al. | 128/287 |
| 4,350,655 | 9/1982 | Hoge | 264/145 |
| 4,352,849 | 10/1982 | Mueller | 428/213 |

(List continued on next page.)

FOREIGN PATENT DOCUMENTS

| | | |
|---|---|---|
| 0247897 | 12/1987 | European Pat. Off. . |
| 0329377 | 8/1989 | European Pat. Off. . |
| 0456044 | 11/1991 | European Pat. Off. . |
| 0 712 892 | 5/1996 | European Pat. Off. . |
| 95/16562 | 6/1995 | WIPO . |
| 95/27005 | 10/1995 | WIPO . |
| 96/19346 | 6/1996 | WIPO . |
| 96/34741 | 11/1996 | WIPO . |
| 97/04955 | 2/1997 | WIPO . |
| 98/04397 | 2/1998 | WIPO . |
| 98/29504 | 7/1998 | WIPO . |

OTHER PUBLICATIONS

Rexene Corporation, Rexflex FPO.
Huntsman Corporation, Rexflex FPO Flexible Polyolefins.
Dr. H. G. Wey, Hëls Aktiengesellchaft, Vestoplast—Amorphous Polyalphaolefins.
Rexene Corporation, Rextac Polymers.
Exxon PE Grades, May 1996 (chart).
"New LLDPEs Offer Combined Properties, Processing Edge", Plastics World, Apr. 1997, p. 8.
"Don't Say 'Metallocene,' Say 'Single–Site'", by Jan. H. Schut, Plastics World, Apr. 1997, p. 27–32.
"Here's the Latest Score on Single Site Catalysts", by Jan H. Schut, Plastics World, Apr., 1997, pp. 41–46.

*Primary Examiner*—Elizabeth M. Cole
*Attorney, Agent, or Firm*—Douglas H. Tulley, Jr.

[57] ABSTRACT

A breathable barrier laminate is disclosed having a first film layer comprising a microporous breathable barrier film; a second film layer comprising a breathable filled film which comprises about 50% to about 70% by weight filler and an amorphous polymer such as an elastomeric ethylene polymer having a density less than 0.89 g/cm³; and a third fibrous layer comprising a breathable outer layer, such as a nonwoven web of spunbonded fibers. The multiple layers can be thermally laminated wherein laminate has a peel strength in excess of 200 grams and a WVTR in excess of 300 g/m²/day.

30 Claims, 2 Drawing Sheets

U.S. PATENT DOCUMENTS

| | | | |
|---|---|---|---|
| 4,364,985 | 12/1982 | Tokuyama et al. | 428/149 |
| 4,376,147 | 3/1983 | Byrne et al. | 428/167 |
| 4,377,616 | 3/1983 | Ashcraft et al. | 428/213 |
| 4,384,024 | 5/1983 | Mitchell et al. | 428/349 |
| 4,386,129 | 5/1983 | Jacoby | 428/215 |
| 4,390,385 | 6/1983 | Ferguson et al. | 156/229 |
| 4,407,986 | 10/1983 | Nomura et al. | 523/200 |
| 4,430,468 | 2/1984 | Schumacher | 524/109 |
| 4,434,258 | 2/1984 | Schumacher et al. | 524/13 |
| 4,438,175 | 3/1984 | Ashcraft et al. | 428/315.5 |
| 4,439,478 | 3/1984 | Ferguson et al. | 428/137 |
| 4,443,511 | 4/1984 | Worden et al. | 428/198 |
| 4,525,407 | 6/1985 | Ness | 428/138 |
| 4,546,029 | 10/1985 | Cancio et al. | 428/141 |
| 4,582,752 | 4/1986 | Duncan | 428/317.9 |
| 4,582,753 | 4/1986 | Duncan | 428/317.9 |
| 4,585,604 | 4/1986 | Okuyama et al. | 264/41 |
| 4,595,629 | 6/1986 | Mays | 428/286 |
| 4,603,174 | 7/1986 | Okada et al. | 525/240 |
| 4,606,970 | 8/1986 | Sharps, Jr. | 428/301 |
| 4,613,643 | 9/1986 | Nakamura et al. | 524/426 |
| 4,672,091 | 6/1987 | Berta | 525/88 |
| 4,681,578 | 7/1987 | Anderson et al. | 604/385 |
| 4,681,793 | 7/1987 | Linman et al. | 428/138 |
| 4,684,568 | 8/1987 | Lou | 428/265 |
| 4,686,257 | 8/1987 | Mitsuno et al. | 524/449 |
| 4,698,372 | 10/1987 | Moss | 521/145 |
| 4,702,954 | 10/1987 | Duncan | 428/213 |
| 4,704,238 | 11/1987 | Okuyama et al. | 264/41 |
| 4,704,323 | 11/1987 | Duncan et al. | 428/286 |
| 4,705,813 | 11/1987 | Ito et al. | 521/92 |
| 4,734,324 | 3/1988 | Hill | 428/317.3 |
| 4,748,070 | 5/1988 | Beehler | 428/198 |
| 4,758,396 | 7/1988 | Crass et al. | 264/145 |
| 4,758,462 | 7/1988 | Park et al. | 428/213 |
| 4,761,324 | 8/1988 | Rautenberg et al. | 428/198 |
| 4,777,073 | 10/1988 | Sheth | 428/155 |
| 4,780,364 | 10/1988 | Wade et al. | 428/315.5 |
| 4,789,699 | 12/1988 | Kieffer et al. | 524/271 |
| 4,791,144 | 12/1988 | Nagou et al. | 521/90 |
| 4,814,124 | 3/1989 | Aoyama et al. | 264/41 |
| 4,824,718 | 4/1989 | Hwang | 428/284 |
| 4,832,886 | 5/1989 | Douglas | 264/41 |
| 4,842,741 | 6/1989 | Coughlin et al. | 210/500.36 |
| 4,857,370 | 8/1989 | Overbergh et al. | 422/34.9 |
| 4,861,652 | 8/1989 | Lippert et al. | 428/284 |
| 4,863,792 | 9/1989 | Mrozinski | 428/315.5 |
| 4,879,078 | 11/1989 | Antoon, Jr. | 264/41 |
| 4,902,553 | 2/1990 | Hwang et al. | 428/156 |
| 4,908,251 | 3/1990 | Iimura et al. | 428/68 |
| 4,909,971 | 3/1990 | Coughlin et al. | 264/45.5 |
| 4,910,639 | 3/1990 | Schloegl et al. | 361/323 |
| 4,921,652 | 5/1990 | Tsuji et al. | 264/41 |
| 4,921,653 | 5/1990 | Aoyama et al. | 264/41 |
| 4,923,650 | 5/1990 | Antoon, Jr. | 264/41 |
| 4,929,303 | 5/1990 | Sheth | 156/209 |
| 4,960,637 | 10/1990 | Biczenczuk | 428/314.4 |
| 4,965,123 | 10/1990 | Swan et al. | 428/314.4 |
| 5,006,394 | 4/1991 | Baird | 428/138 |
| 5,008,296 | 4/1991 | Antoon, Jr. et al. | 521/91 |
| 5,026,591 | 6/1991 | Henn et al. | 428/198 |
| 5,026,592 | 6/1991 | Janocha et al. | 428/204 |
| 5,032,450 | 7/1991 | Rechlicz et al. | 428/196 |
| 5,073,316 | 12/1991 | Bizen et al. | 264/22 |
| 5,091,236 | 2/1992 | Keller et al. | 428/213 |
| 5,110,677 | 5/1992 | Barmore et al. | 428/349 |
| 5,126,197 | 6/1992 | Schinkel et al. | 428/349 |
| 5,126,198 | 6/1992 | Schinkel et al. | 428/349 |
| 5,143,679 | 9/1992 | Weber et al. | 264/288.8 |
| 5,149,332 | 9/1992 | Walton et al. | 604/358 |
| 5,169,712 | 12/1992 | Tapp | 428/315.5 |
| 5,173,235 | 12/1992 | Kamei et al. | 264/154 |
| 5,176,953 | 1/1993 | Jacoby et al. | 428/315.5 |
| 5,204,179 | 4/1993 | Baker et al. | 428/336 |
| 5,204,429 | 4/1993 | Kaminsky et al. | 526/308 |
| 5,208,098 | 5/1993 | Stover | 428/284 |
| 5,209,884 | 5/1993 | Wood, Jr. | 264/41 |
| 5,212,009 | 5/1993 | Peiffer et al. | 428/220 |
| 5,212,246 | 5/1993 | Ogale | 525/240 |
| 5,218,036 | 6/1993 | Kagawa et al. | 524/451 |
| 5,236,625 | 8/1993 | Bardo et al. | 261/24 |
| 5,236,963 | 8/1993 | Jacoby et al. | 521/92 |
| 5,241,031 | 8/1993 | Mehta | 526/348.1 |
| 5,244,716 | 9/1993 | Thornton et al. | 428/198 |
| 5,250,612 | 10/1993 | Hazlitt et al. | 525/53 |
| 5,261,899 | 11/1993 | Visscher et al. | 604/367 |
| 5,263,949 | 11/1993 | Karami et al. | 604/383 |
| 5,272,236 | 12/1993 | Lai et al. | 526/348.5 |
| 5,277,970 | 1/1994 | Schuhmann et al. | 428/323 |
| 5,278,272 | 1/1994 | Lai et al. | 526/348.5 |
| 5,284,540 | 2/1994 | Roth et al. | 156/160 |
| 5,288,791 | 2/1994 | Collier, IV et al. | 524/505 |
| 5,300,365 | 4/1994 | Ogale | 428/461 |
| 5,317,035 | 5/1994 | Jacoby et al. | 521/143 |
| 5,318,842 | 6/1994 | Ogale | 428/349 |
| 5,324,576 | 6/1994 | Reed et al. | 428/288 |
| 5,326,625 | 7/1994 | Schuhmann et al. | 428/215 |
| 5,331,047 | 7/1994 | Giacobbe | 525/88 |
| 5,332,613 | 7/1994 | Taylor et al. | 428/152 |
| 5,372,882 | 12/1994 | Peiffer et al. | 428/34.9 |
| 5,374,696 | 12/1994 | Rosen et al. | 526/126 |
| 5,376,430 | 12/1994 | Swenson et al. | 428/152 |
| 5,382,461 | 1/1995 | Wu | 428/86 |
| 5,385,972 | 1/1995 | Yamamoto et al. | 524/579 |
| 5,397,635 | 3/1995 | Wood, Jr. | 428/314.4 |
| 5,409,761 | 4/1995 | Langley | 428/198 |
| 5,422,172 | 6/1995 | Wu | 428/230 |
| 5,445,862 | 8/1995 | Kaneko et al. | 428/148 |
| 5,445,874 | 8/1995 | Shehata . | |
| 5,451,450 | 9/1995 | Erderly et al. | 428/220 |
| 5,453,318 | 9/1995 | Giacobbe | 428/286 |
| 5,470,639 | 11/1995 | Gessner et al. | 428/152 |
| 5,472,775 | 12/1995 | Obijeski et al. | 428/220 |
| 5,539,124 | 7/1996 | Etherton et al. | 548/402 |
| 5,554,775 | 9/1996 | Krishnamurti et al. | 556/7 |
| 5,582,923 | 12/1996 | Kale et al. | 428/523 |
| 5,595,567 | 1/1997 | King et al. | 604/391 |
| 5,605,735 | 2/1997 | Zehner et al. | 428/100 |
| 5,616,420 | 4/1997 | Yamaoka et al. | 428/515 |
| 5,624,991 | 4/1997 | Harada et al. | 524/451 |
| 5,695,868 | 12/1997 | McCormack | 428/283 |
| 5,882,769 | 3/1999 | McCormack et al. | 428/152 |

BREATHABLE FILLED FILM LAMINATE

FIELD OF THE INVENTION

The present invention relates to filled breathable films. More particularly, the present invention relates to filled breathable films and laminates thereof having high peel strength.

BACKGROUND OF THE INVENTION

There exists a variety of fabrics today which are capable of acting as a barrier to particulate matter, water and other liquids yet which allow water vapor and air to pass therethrough. Such fabrics are commonly referred to as "breathable barriers." Breathable barrier fabrics have been employed in outdoor fabrics, tarpaulins, garments, personal care products, infection control products, as well as numerous other articles. Moreover breathable barrier fabrics are often preferred over non-breathable barrier materials since breathable barrier fabrics allow moisture trapped beneath the fabric to escape as water vapor. Thus, apparel using breathable barrier fabrics is generally more comfortable to wear since the migration of water vapor through the fabric helps to reduce and/or eliminate discomfort resulting from excess moisture trapped against the skin.

While a variety of breathable barrier fabrics are known in the art, one particularly useful breathable barrier comprises stretched filled microporous films. Such films are typically filled with particles or other matter and then crushed or stretched to form a fine pore network which creates tortuous paths through the film. The film pore network allows gas and water vapor to pass through the film while acting as a barrier to liquids and particulate matter. The amount of filler within the film and the degree of stretching is controlled so as to create a network of micro pores of a size and/or frequency to impart the desired level of breathability to the fabric. An exemplary stretched filled film is described in commonly assigned WO Patent Application 95/16562 to McCormack which discloses a stretched filled film comprising a predominantly linear polyolefin polymer, a bonding agent and about 30 to 80% by weight calcium carbonate. The filled polyolefin film can be stretched to impart breathability to the film. The stretched film may then be laminated to a nonwoven web to create a laminate that takes advantage of the strength and integrity of the nonwoven web and the barrier properties of the stretched film.

Thin films, such as those that may result from the stretching or orienting of filled films, are often easily split or torn in the direction of orientation. Thus, as indicated above, stretched-filled films are often laminated to a support layer in order to provide additional strength and integrity to the film. The peel strength of the laminate is desirably strong enough to resist delamination which may result from further processing, transportation and/or storage of the laminate. Often this includes exposure to hot and humid conditions. Moreover, the laminate desirably also resists delamination which may result from mechanical stress applied to the laminate in use. As an example, wear of garments or diapers incorporating the barrier laminate subjects the laminate to stress as a result of abrasion, pulling and other manipulation of the article. In addition to the strain naturally resulting from wear, many articles today employ various fasteners, such as tape or hook and loop systems, which pull on the outer layer thereby creating additional strain on the laminate. Examples of fastening systems are disclosed in commonly assigned U.S. Pat. No. 5,605,735 to Zehner et al.; U.S. Pat. No. 5,019,073 to Roessler et al.; U.S. Pat. No. 5,624,429 to Long et al.; and U.S. patent application Ser. No. 08/534,227 filed Sep. 26, 1995 to Roessler et al. As a result of the pull created by fasteners, many nonwoven/film laminates begin to peel or delaminate, thereby causing the film to separate from the support fabric. In this regard the film becomes considerably more prone to being split or torn once separated from the support fabric. Delamination may therefore ultimately result in a loss of barrier properties, i.e. a leaky product. In addition, even when delamination occurs in areas where the barrier properties are less critical, for example along the edges of a product, the delamination is aesthetically undesirable and gives the appearance of a product of lesser quality. Therefore, breathable barrier laminates having good peel strength are highly desirable.

However, lamination of thin breathable films to one or more supporting layers in a manner to achieve the desired peel strength is particularly difficult without degrading either the barrier properties and/or the breathability of the films. Generally speaking, when thermally bonding two layers of thermoplastic materials together, better lamination or peel strengths may be achieved by increasing the bonding temperature and/or by increasing the overall bond area. Thermal bonding of thin films and a support layer at temperatures necessary to achieve increased peel strengths often create "burn throughs" or pinholes in the film which degrade the barrier properties. This is of course highly undesirable in fabrics where the film is intended to act as a barrier to materials such as urine and other body exudates and an even greater concern where the film is employed as a barrier to hazardous materials such as, for example, blood. In addition, point bonding often destroys the breathability of the fabric within the bond areas, and thus increasing the overall bond area can undesirably lower the breathability of the laminate. Extensive thermal bonding can also undesirably decrease the hand and flexibility of the resulting laminate. Moreover, adhesive lamination of the thin breathable film and support fabric may often likewise suffer from delamination as a result of the physical and mechanical stress experienced by breathable barrier laminates. Furthermore, certain adhesives can decrease the breathability of the laminate and/or undesirably stiffen the laminate.

Thus, there exists a need for a breathable barrier laminate which exhibits good breathability and barrier properties yet which also exhibits excellent peel strength. Moreover, there exists a need for such a breathable barrier laminate which has good hand, is durable and further which may employ a variety of film and laminate structures. Further, there exists a need for such a breathable barrier laminate that may be fabricated by a robust process which is functional under a wide latitude of processing conditions and parameters.

SUMMARY OF THE INVENTION

The aforesaid needs are fulfilled and the problems experienced by those skilled in the art overcome by the breathable barrier laminate of the present invention comprising a breathable base film, a breathable intermediate amorphous polymer layer and a breathable outer fibrous layer bonded thereto. The base film desirably comprises a breathable microporous barrier film having a WVTR of at least 100 g/m²/day. The intermediate layer, having a first and second side, desirably comprises a breathable filled film of a low density ethylene elastomer having a density less than about 0.89 g/cm³ and at least about 50% by weight filler. The first side of the intermediate layer is substantially continuously joined to the base film and the second side is juxtaposed with and bonded to the fibrous layer. The outer fibrous layer is desirably laminated to the second side of the intermediate layer wherein the laminate has a peel strength of at least 200 g and further wherein the entire laminate has a WVTR of at least 100 g/m²/day.

In a further aspect, the low density ethylene elastomer component desirably comprises a copolymer of ethylene and an alpha-olefin polymer such as, for example, a substantially linear polyethylene. Further, the low density ethylene elastomer desirably has a density between about 0.86 g/cm³ and about 0.89 g/cm³. The intermediate layer may further comprise a second polyolefin polymer, such as a second ethylene copolymer. Desirably the low density ethylene elastomer comprises at least about 50% by weight of the polymeric portion of the intermediate filled film.

In a further aspect, the breathable base film can comprise a polyolefin polymer and filler, desirably a filled linear low density polyethylene film that has been stretched to impart breathability to the film. The base film and the intermediate film preferably have a collective basis weight less than about 50 g/m² and further, the intermediate layer desirably comprises less than about 30% of the combined thickness of the base film and intermediate layer. The base film desirably comprises from about 35% to about 65% by weight filler, such as calcium carbonate particles. In a further aspect, the breathable intermediate filler layer desirably has a weight percent filler content which is substantially equal to and/or higher than that of the base film.

In a further aspect, the breathable fibrous layer can comprise a nonwoven fabric. Desirably the fibrous layer comprises a nonwoven web having a basis weight of about 8 g/m² to about 70 g/m², such as propylene polymer fiber spunbond web. The breathable barrier laminate of the present invention desirably has a peel strength in excess of 200 g and even more desirably in excess of 300 g and/or 500 g. Further, the breathable barrier laminate also desirably has a WVTR in excess of 300 g/m²/day, 800 g/m²/day and even 1500 g/m² day. The outer layer can be laminated to the bonding layer by thermally adhering the respective layers together, i.e. melting at least one of the polymers. Suitable methods for laminating the layers includes, but is not limited to, thermal, ultrasonic, infra-red and other like bonding methods. The base film, outer layer and/or the laminate can be either elastic or inelastic.

DEFINITIONS

As used herein the term "nonwoven" fabric or web means a web having a structure of individual fibers or threads which are interlaid, but not in an identifiable manner as in a knitted fabric. Nonwoven fabrics or webs have been formed by many processes such as for example, meltblowing processes, spunbonding processes, hydroentangling, air-laid and bonded carded web processes.

As used herein the term "spunbond fibers" refers to small diameter fibers of molecularly oriented polymeric material. Spunbond fibers may be formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, and U.S. Pat. No. 5,382,400 to Pike et al. Spunbond fibers are generally not tacky when they are deposited onto a collecting surface and are generally continuous. Spunbond fibers are often about 10 microns or greater in diameter. However, fine fiber spunbond webs (having and average fiber diameter less than about 10 microns) may be achieved by various methods including, but not limited to, those described in commonly assigned U.S. patent applications Ser. No. 08/756,426 filed Nov. 26, 1996 to Marmon et al. and Application Ser. No. 08/565,261 filed Nov. 30, 1995 to Pike et al.

As used herein the term "meltblown fibers" means fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers may be continuous or discontinuous, are generally smaller than 10 microns in average diameter, and are generally tacky when deposited onto a collecting surface.

As used herein "multilayer nonwoven laminate" means a laminate of two or more nonwoven layers such as, for example, wherein some of the layers are spunbond and some meltblown such as a spunbond/meltblown/spunbond (SMS) laminate. Examples of multilayer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein, the term "machine direction" or MD means the length of a fabric in the direction in which it is produced. The term "cross machine direction" or CD means the width of fabric, i.e. a direction generally perpendicular to the MD.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible geometrical configurations of the molecule. These configurations include, but are not limited to isotactic, syndiotactic and random symmetries.

As used herein the term "flexible polyolefin" refers to polyolefin materials containing propylene based polymer with controlled regions of atactic polypropylene units to achieve a desired crystallinity such as described in U.S. patent application Ser. No. 08/775,087 filed Dec. 30,1996 entitled "Oriented Polymeric Microporous Films with Flexible Polyolefins and Methods of making the Same" to Hetzler and Jacobs; the entire contents of which are incorporated herein by reference.

As used herein the term "amorphous polymer", when used to describe a bonding layer either as a multilayer film component or separately applied layer, means a thermoplastic polymer such as certain polyolefins with a density in the range of from about 0.85 to about 0.89 and low crystallinity, for example, less than about 30%.

As used herein, "ultrasonic bonding" means a process performed, for example, by passing the fabric between a sonic horn and anvil roll as illustrated in U.S. Pat. No. 4,374,888 to Bornslaeger.

As used herein "point bonding" means bonding one or more layers of fabric at a plurality of discrete bond points. For example, thermal point bonding generally involves passing one or more layers to be bonded between heated rolls such as, for example an engraved pattern roll and a smooth calender roll. The engraved roll is, patterned in some way so that the entire fabric is not bonded over its entire surface, and the anvil roll is usually flat. As a result, various patterns for engraved rolls have been developed for functional as well as aesthetic reasons. One example of a pattern has points and is the Hansen Pennings or "H&P" pattern with about a 30% bond area when new and with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5% when new. Another typical point bonding pattern is the expanded Hansen Pennings or "EHP" bond pattern which produces a 15% bond area when new with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15% when new. Yet another common pattern is the C-Star pattern which has, when new, a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 15% bond area. A further pattern is the "s-weave" pattern having about a 17% bond area when new. Typically, the percent bonding area is less than about 50% and more desirably varies from around 10% to around 30% of the area of the fabric laminate web.

As used herein, the term "barrier" means a film, laminate or other fabric which is relatively impermeable to the transmission of liquids and which has a hydrohead of at least 50 mbar water. Hydrohead as used herein refers to a measure of the liquid barrier properties of a fabric. However, it should be noted that in many applications of barrier fabrics, including those of the present invention, it may be desirable that they have a hydrohead value greater than about 80 mbar, 150 mbar or even 300 mbar water.

As used herein, the term "breathable" refers to a material which is permeable to water vapor having a minimum WVTR of about 100 g/m²/24 hours. The WVTR of a fabric is water vapor transmission rate which, in one aspect, gives an indication of how comfortable a fabric would be to wear. WVTR (water vapor transmission rate) is measured as indicated below and the results are reported in grams/square meter/day. However, often applications of breathable barriers desirably have higher WVTRs and breathable barriers of the present invention can have WVTRs exceeding about 300 g/m²/day, 800 g/m²/day, 1500 g/m²/day or even exceeding 3000 g/m²/day.

As used herein the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. As used herein the term "multicomponent fibers" refers to fibers which have been formed from at least two polymers extruded from separate extruders but spun together to form one fiber. Multicomponent fibers are also sometimes referred to as conjugate or bicomponent fibers. The polymers of a multicomponent fiber are arranged in substantially constantly positioned distinct zones across the cross-section of the fiber and extend continuously along the length of the fiber. The configuration of such a fiber may be, for example, a sheath/core arrangement wherein one polymer is surrounded by another or may be a side by side arrangement, a pie arrangement or an "islands-in-the-sea" type arrangement. Multicomponent fibers are taught in U.S. Pat. No. 5,108,820 to Kaneko et al., U.S. Pat. No. 4,795,668 to Krueger et al. and U.S. Pat. No. 5,336,552 to Strack et al. Conjugate fibers are also taught in U.S. Pat. No. 5,382,400 to Pike et al. and may be used to produce crimp in the fibers by using the differential crystallization properties of the two (or more) polymers. Crimped fibers may also be produced by mechanical means and by the process of German Patent DT 25 13 251 A1. For two component fibers, the polymers may be present in ratios of 75/25, 50/50, 25/75 or any other desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "blend" means a mixture of two or more polymers while the term "alloy" means a sub-class of blends wherein the components are immiscible but have been compatibilized.

As used herein the term "biconstituent fibers" or "multiconstituent" refers to fibers which have been formed from at least two polymers extruded from the same extruder as a blend. The term "blend" is defined above. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, ISBN 0-306-30831-2, at pages 273 through 277.

As used herein, the term "bonding window" means the range of temperature of the mechanism, e.g. a pair of heated bonding rolls, used to bond the nonwoven fabric together, over which such bonding is successful.

As used herein, the term "scrim" means a lightweight fabric used as a backing material. Scrims are often used as the base fabric for coated or laminated products.

As used herein, the term "garment" means any type of non-medically oriented apparel which may be worn. This includes industrial work wear and coveralls, undergarments, pants, shirts, jackets, gloves, socks, and the like.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

As used herein, the term "personal care product" means diapers, training pants, absorbent underpants, adult incontinence products, and feminine hygiene products.

As used herein, the term "protective cover" means a cover for vehicles such as cars, trucks, boats, airplanes, motorcycles, bicycles, golf carts, etc., covers for equipment often left outdoors like grills, yard and garden equipment (mowers, roto-tillers, etc.) and lawn furniture, as well as floor coverings, table cloths and picnic area covers.

DETAILED DESCRIPTION OF THE INVENTION

Figure 1:
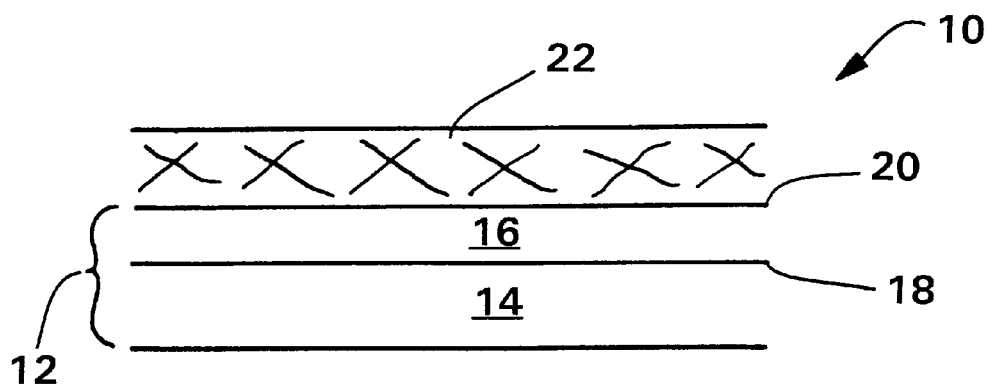
FIG. 1 is a cross-sectional view of a breathable barrier laminate of the present invention.

The present invention is directed to a breathable barrier laminate 10 comprising, in reference to FIG. 1, a multilayer film 12 and an outer fibrous layer 22. The multilayer film 12 can comprise a first breathable base layer 14 and an adjacent breathable intermediate layer 16. The breathable intermediate layer 16 has a first side 18 and a second side 20. The outer fibrous layer 22 is attached to the second side 20 of breathable intermediate layer 16 and the breathable base layer 14 is attached to the first side 18 of the breathable intermediate layer 16.

The breathable base layer comprises a breathable film. For example, the breathable base layer can comprise a microporous film having a WVTR greater than 100 $g/m^2/$day, desirably having a WVTR in excess of 300 $g/m^2/day$, 800 $g/m^2/day$, 1500 $g/m^2/day$ or even 3000 $g/m^2/day$. The breathable base layer 12 can be formed by any one of various methods known in the art. Desirably the first breathable barrier layer comprises a stretched-filled film which includes a thermoplastic polymer and filler. These (and other) components can be mixed together, heated and then extruded into a monolayer or multilayer film. The filled film may be made by any one of a variety of film forming processes known in the art such as, for example, by using either cast or blown film equipment. Preferably the breathable base film and breathable intermediate layer are simultaneously made such as, for example, formed by co-extrusion. As an example, methods of forming multilayer films are disclosed in U.S. Pat. No. 4,522,203; U.S. Pat. No. 4,734,324 and WO 96/19346; the entire contents of which are incorporated herein by reference.

In a preferred embodiment the base layer is a breathable barrier comprising a thin film made from a thermoplastic polymer which was stretched in at least one direction, thereby reducing the film gauge or thickness. Thermoplastic polymers used in the fabrication of the films of the present invention include, but are not limited to, polyolefins including homopolymers, copolymers, terpolymers and blends thereof. In addition, flexible polyolefins or "polyolefin based" films are also believed suitable for use in the present invention. For purposes of the present invention a polymer is considered to be "polyolefin-based" if the polymeric portion of the film, exclusive of any filler materials, has at least 50 weight percent polyolefin. Additional film forming polymers which may be suitable for use with the present invention, alone or in combination with other polymers, include ethylene vinyl acetate (EVA), ethylene ethyl acrylate (EEA), ethylene acrylic acid (EAA), ethylene methyl acrylate (EMA), ethylene normal butyl acrylate (EnBA), polyester, polyethylene terephthalate (PET), nylon, ethylene vinyl alcohol (EVOH), polystyrene (PS), polyurethane (PU), polybutylene (PB), and polybutylene terephthalate (PBT). However, polyolefin polymers are preferred such as, for example, polymers of ethylene and propylene as well as copolymers, terpolymers and blends thereof; examples include, but are not limited to, linear low density polyethylene (LLDPE) and ethylene-propylene copolymer blends.

In addition to the thermoplastic polymer, breathable stretched-filled films can further include a filler to impart breathability to the film upon stretching. As used herein a "filler" is meant to include particulates and/or other forms of materials which can be added to the film polymer extrusion blend which will not chemically interfere with or adversely affect the extruded film and further which can be uniformly dispersed throughout the film. Generally the fillers will be in particulate form with average particle sizes in the range of about 0.1 to about 10 microns, desirably from about 0.1 to about 4 microns. As used herein the term "particle size" describes the largest dimension or length of the filler. Both organic and inorganic fillers are contemplated for use with the present invention provided they do not interfere with the film forming process and/or subsequent laminating processes. Examples of fillers include calcium carbonate ($CaCO_3$), various clays, silica ($SiO_2$), alumina, barium sulfate, talc, magnesium sulfate, titanium dioxide, zeolites, aluminum sulfate, cellulose-type powders, diatomaceous earth, gypsum, magnesium sulfate, magnesium carbonate, barium carbonate, keaolin, mica, carbon, magnesium oxide, aluminum hydroxide, pulp powder, wood powder, cellulose derivatives, polymeric particles, chitin and chitin derivatives. The filler particles may optionally be coated with a fatty acid, such as stearic acid or behenic acid, and/or other material in order to facilitate the free flow of the particles (in bulk) and their ease of dispersion into the polymer. In reference to the base film, the filled film will usually contain at least about 35% filler based upon the total weight of the base film layer, more desirably from about 45% to about 65% by weight filler.

In addition, the base film may optionally include one or more stabilizers. Desirably the filled film includes an antioxidant such as, for example, a hindered phenol stabilizer. Commercially available anti-oxidants include, but are not limited to, IRGANOX™ E 17 (α-tocopherol) and IRGANOX™ 1076 (octodecyl 3,5-di-tert-butyl-4-hydroxyhydrocinnamate) which are available from Ciba Specialty Chemicals of Terrytown, N.Y. Desirably about 100 to 1000 ppm of the stabilizer is added to the base polymer(s) prior to extrusion. (Parts per million is in reference to the entire weight of the filled film.) In addition, other stabilizers or additives which are compatible with the film forming process, stretching and any subsequent lamination steps may also be employed with the present invention. For example, additional additives may be added to impart desired characteristics to the film such as, for example, melt stabilizers, processing stabilizers, heat stabilizers, light stabilizers, heat aging stabilizers and other additives known to those skilled in the art. Generally, phosphite stabilizers (e.g. IRGAFOS™ 168 available from Ciba Specialty Chemicals of Terrytown, N.Y and DOVERPHOS™ available from Dover Chemical Corp. of Dover, Ohio) are good melt stabilizers whereas hindered amine stabilizers (e.g. CHIMASSORB™ 944 and 119 available from Ciba Specialty Chemicals of Terrytown, N.Y) are good heat and light stabilizers.

The breathable intermediate layer 16 comprises at least two components, including an amorphous polymer component and filler. The polymeric component desirably comprises a low density ethylene elastomer which includes ethylene copolymers having a density less than about 0.89 g/cc, desirably from about 0.86 g/cc to about 0.88 g/cc and even more desirably about 0.87 g/cc. Desirably the ethylene elastomers comprise substantially linear polyethylene. The ethylene elastomer preferably comprises at least about 50% by weight of the polymeric portion of the intermediate layer, and more desirable from about 70% to 100% by weight. Preferably the ethylene elastomer comprises a polymer wherein the ethylene monomers are polymerized with an alpha-olefin such that the resulting polymer composition has a narrow molecular weight distribution ($\overline{M}_w/\overline{M}_n$) of about 2, homogeneous branching and controlled long chain branching. Suitable alpha-olefins include, but are not limited to, 1-octene, 1-butene, 1-hexene and 4-methyl-pentene. Exemplary polymers include those made by "metallocene", "constrained geometry" or "single-site" catalysts such as those described in U.S. Pat. No. 5,472,775 to Obijeski et al.; U.S. Pat. No. 5,451,450 to Erderly et al.; U.S. Pat. No. 5,204,429 to Kaminsky et al.; U.S. Pat. No. 5,539,124 to Etherton et al.; and U.S. Pat. No. 5,554,775 to Krishnamurti et al.; the entire contents of which are incorporated herein by reference.

The metallocene process generally uses a metallocene catalyst which is activated, i.e. ionized, by a co-catalyst. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow. However, numerous other metallocene, single-site and/or similar catalyst systems are known in the art; see for example, *The Encyclopedia of Chemical Technology*, Kirk-Othemer, Fourth Edition, vol. 17, Olefinic Polymers, pp. 765–767 (John Wiley & Sons 1996).

Regarding metallocene based elastomeric polymers, U.S. Pat. No. 5,204,429 to Kaminsky et al. describes a process which may produce elastic copolymers from cycloolefins and linear olefins using a catalyst which is a stereorigid chiral metallocene transition metal compound and an aluminoxane. The polymerization is carried out in an inert solvent such as an aliphatic or cycloaliphatic hydrocarbon such as toluene. U.S. Pat. Nos. 5,278,272 and 5,272,236, both to Lai et al., assigned to Dow Chemical and entitled "Elastic Substantially Linear Olefin Polymers" describe polymers having particular elastic properties, the entire contents of which are incorporated herein by reference. Suitable low density ethylene elastomers are commercially available from Dow Chemical Company of Midland, Mich. under the trade name AFFINITY™, including AFFINITY™ EG8200 (5 MI), XU 58200.02 (30 MI), XU 58300.00 (10 MI) and from Exxon Chemical Co. of Houston, Tex., under the trade name EXACT™ 4049 (4.5 MI, 0.873 g/cc); 4011 (2.2 MI, 0.888 g/cc); 4041 (3 MI, 0.878 g/cc; 4006 (10 MI, 0.88 g/cc).

In addition to the amorphous polymer, the polymeric component of the intermediate layer may further comprise up to about 50%, by weight, of one or more additional polymers. The intermediate layer may thus also comprise additional thermoplastic polymers, desirably polyolefins and even more desirably comprising blends and/or copolymers of ethylene and/or propylene. Exemplary polymers include, but are not limited to, polyethylene (homopolymer), linear low density polyethylene, EVA, EMA, EnBA, flexible polyolefins and/or ethylene-propylene copolymers. In one embodiment, the low density ethylene elastomer is blended with a second polyethylene polymer having a density ranging from about 0.90 to about 0.95 g/cm$^3$. Additional commercially available polyolefin polymer components include, but are not limited to, Himont Catalloy Polymer KS350, KS357 and KS359. Himont Catalloy polymer is an olefinic multistep reactor product wherein an amorphous ethylene propylene random copolymer is molecularly dispersed in a predominantly semicrystalline high propylene monomer/ low ethylene monomer continuous matrix, an example of which is described in U.S. Pat. No. 5,300,365 to Ogale. In addition, the intermediate layer may also include hot melt adhesive resins which desirably have a melt viscosity of 100,000 mPa•sec or greater. Commercially available amorphous polyolefins used in hot melt adhesives suitable for use with the present invention include, but are not limited to, REXTAC™ ethylene-propylene APAO E-4 and E-5 and butylene-propylene BM-4, BH-5, and 2503-3A from Huntsman Corporation of Salt Lake City, Utah and VESTOPLAST™ 792 from Hüls AG of Marl, Germany. These amorphous polyolefins are commonly synthesized on a Ziegler-Natta supported catalyst and an alkyl aluminum co-catalyst and the olefin, such as propylene, is polymerized in combination with varied amounts of ethylene, 1-butene, 1-hexane, or other materials to produce a predominantly atactic hydrocarbon chain. Desirably the hot melt adhesive resins likewise have a density less than 0.89 g/cm$^3$ and also a low $T_g$ (below about −10° C.) in order to improve flexibility and strength.

In addition, the polymeric component of the intermediate layer may further comprise additional additives or stabilizers such as those discussed above with regard to the breathable base layer. Further, the polymeric component may further include various extenders, waxes and other additives. In this regard, in processing co-extruded films it is preferable that the additional polymers have a similar melt viscosity greater than 100,000 mPa•sec. The melt viscosity of the component may be varied by addition of extenders and waxes as is known to those skilled in the art.

The filler component of the intermediate layer can comprise filler similar in type and content as those discussed with regard to the breathable stretch-filled films discussed above with regard to the base film. Where the breathable base layer comprises a filled film, desirably the intermediate layer comprises at least about the same weight % of filler, and even more desirably contains a weight % of filler greater than that of the breathable base layer. Desirably the breathable intermediate layer comprises at least about 45% by weight filler, and even more desirably from about 50% to about 65% by weight filler.

The multilayer film 12, prior to stretching, desirably has a basis weight of less than about 100 grams per square meter (g/m$^2$) and even more desirably less than about 60 g/m$^2$. Upon stretching the multilayer film desirably has a basis weight of less than 60 g/m$^2$ and even more desirably between about 15 and 35 g/m$^2$. Typically such lower basis weight films have a thickness of about 15 microns to about 30 microns. The base film desirably comprises from about 50% to about 98% of the multilayer film thickness and the intermediate filled film desirably comprises from about 2% up to about 50%, more desirably from about 5% up to about 20%, of the total thickness of the multilayer film.

The fibrous layer may comprise any breathable material capable of being laminated to the multilayer film and providing the desired support. The fibrous layer may comprise, as an example, nonwoven webs, multilayer nonwoven laminates, scrims, woven fabrics and/or other like materials. Desirably the support fabric comprises one or more layers of spunbonded and/or meltblown fiber webs. The composition of the thermoplastic polymer may be selected as desired to achieve a material having the desired properties, i.e. hand, aesthetics, tensile strength, cost, abrasion resistance, hook engagement, etc. Further, the fibrous layer may further be treated such as, for example, by embossing, hydroentangling, mechanically softening, printing or treated in another manner in order to achieve the desired aesthetics, hand or other characteristics. In this regard it is possible to emboss various attractive patterns within nonwoven webs, which is particularly desirably in many articles such as, for example, for an outer cover of an infant diaper. In one embodiment the outer layer may comprise about a 10 g/m$^2$ to about 70 g/m$^2$ web of polypropylene spunbond fibers having a pattern printed upon and/or embossed therein and even more desirably a 10 g/m$^2$ to about 30 g/m$^2$ web.

Figure 2:
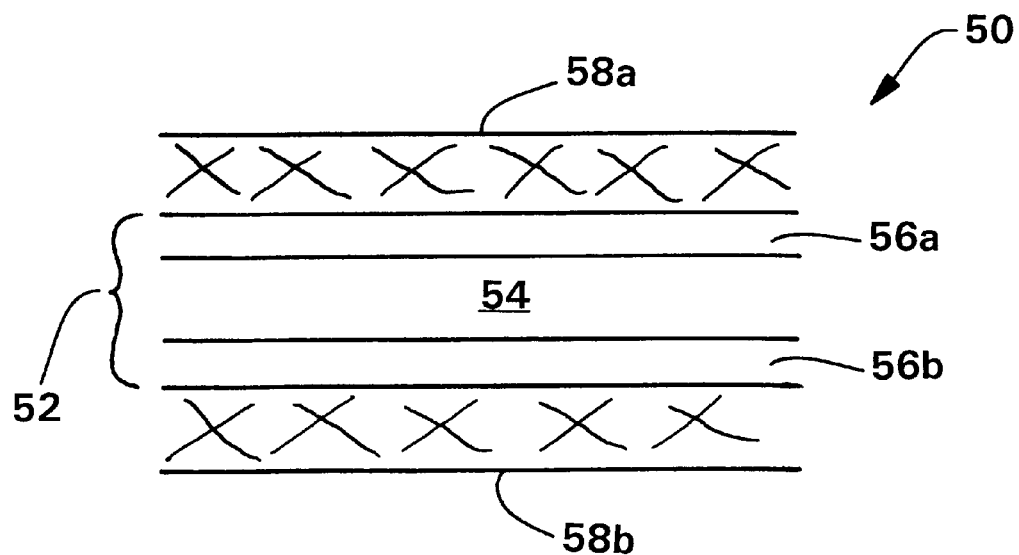
FIG. 2 is a cross-sectional view of a breathable barrier laminate of the present invention.

In a further aspect of the invention and in reference to FIG. 2, the breathable barrier laminate 50 may comprise a multilayer film 52 and outer layers 58a and 58b laminated to opposed sides of the multilayer film 52. The outer layers may comprise materials similar to those discussed above with regard to the outer fibrous layer. When the multilayer film 52 is laminated on both sides it may often be desirable that the multilayer film 52 comprise at least a first breathable base film 54 and breathable intermediate layers 56a and 56b on opposed sides of the base layer 54. Desirably, the intermediate layers 56a and 56b are bonded to the base film 54 on a first side and bonded to the respective outer layers 58a and 58b on the second side. The composition of the base film 54 corresponds to the breathable base layer 14 discussed above and the composition of the intermediate layers 56a and 56b can correspond to the intermediate layer 16 discussed above. However, where the multilayer film comprises two intermediate films it is desirable that the two films collectively not comprise more than about 50% of the total thickness of the multilayer film and preferably together comprise from about 5 to about 20% of the total thickness of the multilayer film.

Figure 3:
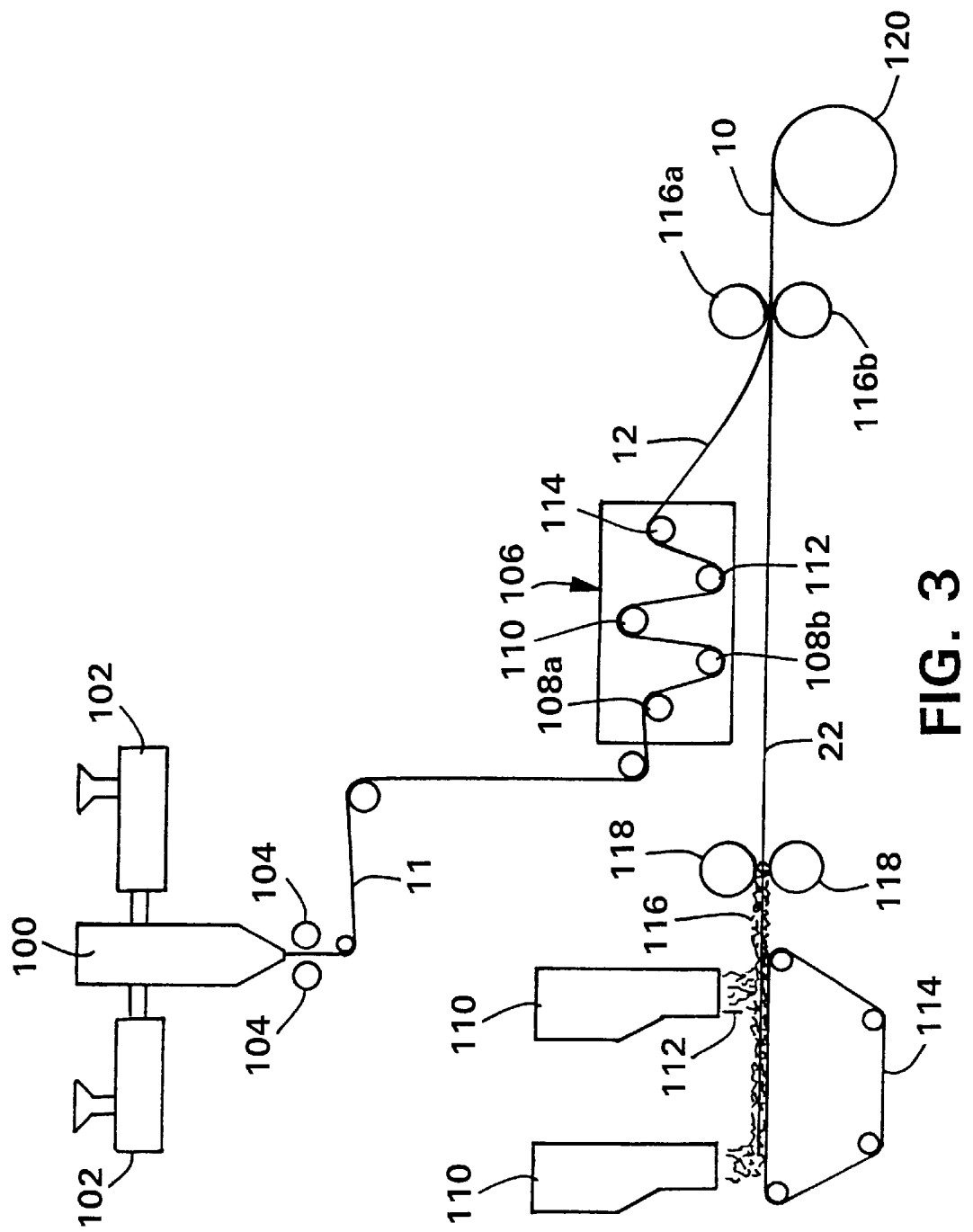
FIG. 3 is a schematic diagram of a process line for making a breathable barrier laminate of the present invention.

In reference to FIG. 3, a schematic diagram of a process line for fabricating breathable barrier laminates of the present invention. Referring to FIG. 3, the multilayer film 11 is formed from a co-extrusion film apparatus 100 such as a cast or blown unit as was previously described above. Typically the apparatus 100 will include two or more polymer extruders 102. The unstretched multilayer film 11 is extruded into a pair of nip or chill rollers 104 one of which may be patterned so as to impart an embossed pattern to the newly formed multilayer film 11. Using a two layer film construction such as shown in FIG. 1, the unstretched multilayer film 11 can have a basis weight less than about 100 g/m$^2$ and more desirably a basis weight of about 60 g/m$^2$ From the co-extrusion film apparatus 100 the unstretched film 11 is directed to a film stretching unit 106 such as a machine direction orienter which may be a commercially available device from vendors such as the Marshall and Williams Company of Providence, R.I. Such an apparatus 106 has a plurality of preheat and stretching rollers which stretch and thin the unstretched multilayer film 11 in the machine direction of the film which is the direction of travel of the film 11 through the process. The film can be stretched in either a single or multiple stretching operations. Further, the film could also be stretched in multiple directions (e.g. biaxially stretched). With regard to FIG. 3, heated rollers 108a and 108b may act as pre-heat rolls. Slow roll 110 is also heated and travels at a circumferential speed slower than that of fast roll 112. The different speeds of the adjacent rollers act to stretch the multilayer film 11. After stretching the film may be allowed to slightly retract and/or be further heated or annealed by one or more heated rollers, such as by heated anneal roll 114. It may often be desirable to heat the multilayer film using a heated roll which is above the melting point of the amorphous polymer component within the intermediate layer. Thus, when using heated rolls above these temperatures, the heated rollers should contact the opposed surface (e.g. the breathable base film). After exiting the film stretching unit 106 the stretched multilayer film 12 desirably has a basis weight less than approximately 60 g/m2, and even more desirably having a basis weight from about 15 to about 35 g/m$^2$.

The multilayer film 12 is attached to one or more outer layers, such as fibrous layer 22, to form a multilayer film/nonwoven laminate 10. Referring again to FIG. 3, a conventional fibrous nonwoven web forming apparatus 110, such as a pair of spunbond machines, can be used to form the outer fibrous layer 22. The long, essentially continuous spunbond fibers 112 are deposited onto a forming wire 114 as an unbonded web 116 and may then sent through a pair of compaction and/or bonding rolls 118 to add sufficient integrity to the web for further processing. Once the multilayer film 11 has been sufficiently thinned and the fibrous layer 22 has been formed, the two layers can be brought together and point bonded to one another using a bonder such as pair of heated bonding rolls 116. The bonding rolls 116 are desirably heated and at least one of the rolls may be patterned to create a discrete bond pattern with a prescribed bond surface area for the resulting laminate 10. Generally, the maximum bond point surface area for one side of the laminate 126 should not exceed about 50 percent of the total surface area of said side of the laminate, and desirably comprises between about 5 and 30% of the total surface area. There are numerous discrete bond patterns which may be used in connection with the present invention. Such as, for example, the c-star pattern as referenced above regarding point bonding and also those described in Brock et al., U.S. Pat. No. 4,041,203. Once the laminate 10 exits the bonding or laminating roll 116, it may be wound up into a winder roll 120. Alternatively, the laminate 10 may continue in-line for further processing and/or conversion.

The process shown in FIG. 3 also may be used to create a multilayer laminate 50 such as is shown in FIG. 2 of the drawings. Feeding a second fibrous layer into the laminating rolls on a side of the multilayer film opposite that of the first fibrous layer allows formation of the laminate 50. Supply of the first and/or second support layer may be provided by a pre-formed roll or may be formed directly in-line. In addition, maintaining heated rolls contacting the intermediate layer below the melting temperature of the amorphous polymer will help prevent the film from adhering to the stretching unit.

The barrier laminates of the present invention may be used to either make or comprise a component of protective covers, infection control products, personal care products, garments and other articles that desirably have barrier properties and breathability. As examples thereof, the barrier laminates may be used as follows: as back sheet or an outer cover in a diaper or adult incontinence garments such as described in U.S. Pat. No. 5,415,644 to Enloe or in surgical gowns such as described in U.S. Pat. No. 4,823,404 to Morrell et al.

Tests

Hydrohead: A measure of the liquid barrier properties of a fabric is the hydrohead test. The hydrohead test determines the height of water or amount of water pressure (in millibars) that the fabric will support before liquid passes therethrough. A fabric with a higher hydrohead reading indicates it has a greater barrier to liquid penetration than a fabric with a lower hydrohead. The hydrohead can be performed according to Federal Test Standard 191A, Method 5514. The hydrohead data cited herein was obtained using a test similar to the aforesaid Federal Test Standard except modified as noted below. The hydrohead was determined using a hydrostatic head tester available from Mario Enterprises, Inc. of Concord, N.C. The specimen is subjected to a standardized water pressure, increased at a constant rate until the first sign of leakage appears on the surface of the fabric in three separate areas. (Leakage at the edge, adjacent clamps is ignored.) Unsupported fabrics, such as a thin film, can be supported to prevent premature rupture of the specimen.

Melt Index: The melt index (MI) is a measure of the viscosity of a polymer. The MFR is expressed as the weight of material which flows from a capillary of known dimensions under a specified load or shear rate for a measured period of time and is measured in grams/10 minutes at 190° C. and load of 2160 g according to ASTM test 1238-90b.

WVTR: The water vapor transmission rate (WVTR) for the sample materials was calculated in accordance with ASTM Standard E96-80. Circular samples measuring three inches in diameter were cut from each of the test materials and a control which was a piece of CELGARD™ 2500 film from Hoechst Celanese Corporation of Sommerville, N.J. CELGARD™ 2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (32° C.) or 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed an immediately returned to the oven. After 24 hours, the pans were removed from the oven and weighed again. The preliminary test water vapor transmission rate values were calculated with Equation (I) below:

$$\text{Test WVTR} = (\text{grams weight loss over 24 hours}) \times 315.5 \text{ g/m}^2/24 \text{ hours} \quad (I)$$

The relative humidity within the oven was not specifically controlled.

Under the predetermined set conditions of 100° F. (32° C.) and ambient relative humidity, the WVTR for the CELGARD™ 2500 control has been defined to be 5000 grams per square meter for 24 hours. Accordingly, the control sample was run with each test and the preliminary test values were corrected to set conditions using Equation (II) below:

$$\text{WVTR} = (\text{Test WVTR/control WVTR}) \times (5000 \text{ g/m}^2/24 \text{ hours}) \quad (II)$$

Peel test: In peel or delamination testing a laminate is tested for the amount of tensile force which will pull the layers of the laminate apart. Values for peel strength are obtained using a specified width of fabric, clamp jaw width and a constant rate of extension. For samples having a film side, the film side of the specimen is covered with masking tape or some other suitable material in order to prevent the film from ripping apart during the test. The masking tape is on only one side of the laminate and so does not contribute to the peel strength of the sample. This test uses two clamps, each having two jaws with each jaw having a facing in contact with the sample, to hold the material in the same plane, usually vertically, separated by 2 inches to start. The sample size is 4 inches wide by as much length as necessary to delaminate enough sample length. The jaw facing size is 1 inch high by at least 4 inches wide, and the constant rate of extension is 300 mm/min. The sample is delaminated by hand a sufficient amount to allow it to be clamped into position and the clamps move apart at the specified rate of extension to pull the laminate apart. The sample specimen is pulled apart at 180° of separation between the two layers and the peel strength reported as an average of peak load in grams. Measurement of the force is begun when 16 mm of the laminate has been pulled apart and continues until a total of 170 mm has been delaminated. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or the Thwing-Albert Model INTELLECT II available from the Thwing-Albert Instrument Co., 10960 Dutton Rd., Phila., Pa. 19154, may be used for this test. Results are reported as an average of three specimens and may be performed with the specimen in the cross direction (CD) or the machine direction (MD).

EXAMPLE 1

A 55 g/m² multilayer film was formed by co-extrusion. The bonding layer comprised 55% stearic acid coated SUPERCOAT™ $CaCO_3$, 45% by weight Dow AFFINITY™ EG 8200 low density elastomeric polyethylene (metallocene-catalyzed, 0.87 g/cm³, melt index of 5.0 g). The base layer comprised 50% stearic acid coated SUPERCOAT™ $CaCO_3$; 45% DOWLEX™ NG 3310 linear low density polyethylene (0.918 g/cm³, melt index of 3.5 g); 5% Dow 4012 LDPE (0.916 g/cm³, melt index of 12 g) and B900 stabilizer available from Ciba-Geigy. The intermediate layer comprised about 10% of the total film thickness.

The co-extruded multilayered film was stretched, in the machine direction, in a single-zone stretching operation using an MDO unit. The multilayer film was stretched 384% of its original length. Prior to stretching the film was pre-heated by a series of "pre-heat" rolls at 120° F., the slow roll was at 150° F. and the fast roll at 70° F. The stretched multilayer film was annealed over an additional roll, without additional tensioning force, at 180° F. The annealed film was then fed into a nip of a thermal point bonder along with a nonwoven web of propylene polymer spunbonded fibers.

The nonwoven web comprised a 20 g/m² (0.6 osy) of about 2.0 denier spunbonded fibers comprising a propylene copolymer (3.5% ethylene). The nonwoven web was itself thermally point bonded with an s-weave pattern prior to entering the nip with the stretched film. The bonded nonwoven web and stretched film were laminated together using a heated patterned roll at 200° F. and a smooth steel anvil roll at 190° F. with a nip pressure of 50 psi. The patterned roll employed a baby object pattern which imparts about a 15% bond area to the laminate.

The resulting laminate had a basis weight of 42 g/m², an MD peel strength of 307 g (a destructive delamination), an unsupported hydrohead of 88 mbar and a WVTR of 1195 g/m²/day.

EXAMPLE 2

A 55 g/m² cast "AB" film was formed by co-extrusion. The bonding layer comprised 60% stearic acid coated SUPERCOAT™ CaCO₃ available from English China Clay Co. of Sylacauga, Ala.; 20% by weight Dow AFFINITY™ EG 8200 low density elastomeric polyethylene (0.87 g/cm³, 5 MI); and 20% VESTOPLAST™ 792 (amorphous propene-rich polyalphaolefin, 0.865 g/cc, melt viscosity at 190° C. of 125,000 mPa•sec according to DIN 53019) available from Hüls America, Inc. of Somerset, N.J. The base layer comprised 50% stearic acid coated SUPERCOAT™ CaCO₃; 45% DOWLEX™ NG 3310 linear low density polyethylene (0.916 g/cm³, 3.5 MI); and 5% Dow 4012 LDPE (0.916 g/cm³, 12 MI). The outer or bonding layer comprised about 10% of the combined thickness of the base film and bonding layer.

The co-extruded multilayered film was stretched, in the machine direction, in a single-zone stretching operation using an MDO unit. The multilayer film was stretched 380% of its original length. Prior to stretching the film was pre-heated by a series of pre-heat rolls at 120° F.; the slow roll was at 150° F. and the fast roll at 70° F. The stretched multilayer film was annealed over an additional roll, without additional tensioning force, at 180° F. The annealed film was then fed into a nip of a thermal point bonder along with a nonwoven web of propylene polymer spunbonded fibers. The nonwoven web comprised a 20 g/m² (0.6 osy) of 2.0 denier spunbonded fibers comprising propylene copolymer (3.5% ethylene). The nonwoven web was itself thermal point bonded with an s-weave pattern prior to entering the nip with the stretched film. The bonded nonwoven web and stretched film were laminated together using a heated patterned roll at 200° F. and a smooth steel anvil roll at 190° F. with a nip pressure of 50 psi. The patterned roll employed a baby object pattern which imparts about a 15% bond area to the laminate.

The resulting laminate had a basis weight of 39 g/m², an MD peel strength of 1340 g (a destructive delamination), an unsupported hydrohead of 92 mbar and a WVTR of 272 g/m²/day.

While various patents and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A breathable barrier laminate comprising:
    a breathable base film comprising a thermoplastic polymer, said base film comprising a microporous olefin polymer film having a WVTR of at least 300 g/m²/day;
    a breathable intermediate microporous film comprising an amorphous polymer and at least about 50% by weight filler, wherein said amorphous polymer comprises a copolymer of ethylene and an alpha-olefin and has a density less than 0.89 g/cm³ and further wherein said intermediate film has a first and second side wherein said first side is bonded to said base film; and
    a breathable fibrous layer bonded to the second side of said intermediate film wherein said laminate has a peel strength of at least 200 g and further wherein said laminate has a WVTR of at least about 300 g/m²/day and a hydrohead of at least 50 mbar.

2. The breathable barrier laminate of claim 1 wherein said ethylene polymer comprises a copolymer of ethylene and an alpha-olefin selected from the group of 1-octene, 1-hexane, 1-butene and 4-methyl-pentene.

3. The breathable barrier laminate of claim 1 wherein said amorphous polymer of the intermediate film comprises a substantially linear polyethylene.

4. The breathable barrier laminate of claim 1 wherein said base film comprises a polyethylene polymer having a density greater than about 0.90 g/m².

5. The breathable barrier laminate of claim 1 wherein said amorphous polymer of said intermediate film comprises an ethylene elastomer having a density between about 0.86 g/cm³ and 0.89 g/cm³ and further wherein said intermediate film comprises from 1 to about 50% by weight of a second polyolefin polymer.

6. The breathable barrier laminate of claim 5 wherein said second polyolefin polymer comprises a polyethylene polymer having a density greater than 0.90 g/cm³.

7. The breathable barrier of claim 1 wherein said base film and said intermediate film have a collective basis weight less than 60 g/m² and wherein said intermediate layer comprises less than about 20% of the combined thickness of said base film and said intermediate film.

8. The breathable barrier laminate of claim 1 wherein said intermediate layer comprises from about 50% to about 65% by weight filler and wherein the intermediate layer comprises less than 30% of the total thickness of the intermediate film and the base film.

9. The breathable laminate of claim 8 wherein said base film comprises a polyolefin polymer and from about 35% to about 65% by weight filler.

10. The breathable laminate of claim 9 wherein said base film comprises a polyethylene polymer and filler.

11. The breathable laminate of claim 10 wherein said intermediate film has a higher weight percent filler content than said base film.

12. The breathable laminate of claim 10 wherein said base film comprises an ethylene polymer having a density in excess of 0.90 g/cm³.

13. The breathable laminate of claim 12 wherein said laminate has a WVTR in excess of 800 g/m² day.

14. The breathable laminate of claim 7 wherein the laminate has a peel strength in excess of 300 g.

15. The breathable laminate of claim 12 wherein said laminate has a peel strength in excess of 500 g.

16. The breathable barrier laminate of claim 5 wherein said base film comprises a linear low density ethylene polymer having a density in excess of 0.90 g/cm³ and wherein said laminate is point bonded and has a peel strength in excess of 300 g.

17. The breathable barrier laminate of claim 16 wherein said fibrous layer comprises a nonwoven web of propylene polymer fibers.

18. The breathable laminate of claim 17 wherein said nonwoven web comprises spunbond fibers.

19. The breathable laminate of claim 12 wherein said fibrous layer comprises a nonwoven web of propylene polymer fibers and wherein said laminate is point bonded and has a peel strength in excess of about 300 g.

20. The breathable laminate of claim 7 wherein the collective basis weight of said base film and intermediate film is less than about 35 g/m$^2$ and wherein said laminate has a peel strength in excess of 500 g.

21. The breathable laminate of claim 1 wherein the collective basis weight of said base film and intermediate film is less than about 35 g/m$^2$ and wherein said laminate has a peel strength in excess of 300 g and a WVTR in excess of 800 g/m$^2$/day.

22. The breathable laminate of claim 1 wherein said intermediate film comprises from 50% to about 70% filler and wherein said intermediate layer further contains a second ethylene copolymer.

23. The breathable laminate of claim 22 wherein said second ethylene copolymer is selected from the group of ethylene-vinyl acetate, ethylene-n-methyl acrylate, ethylene butyl acetate, ethylene-propylene and ethylene-alphaolefin copolymers.

24. The breathable laminate of claim 1 wherein said laminate has a WVTR in excess of 800 gm$^2$/day.

25. The breathable laminate of claim 24 wherein said laminate has a peel strength in excess of 500 g.

26. The breathable barrier laminate of claim 22 wherein said intermediate film is less than about 15% of the combined thickness of said base film and said intermediate film and further wherein said base film and intermediate film have a combined basis weight less than 35 g/m$^2$.

27. The breathable barrier laminate of claim 1 wherein said breathable fibrous layer comprises a nonwoven web and wherein said intermediate film and nonwoven web are bonded by a plurality of discrete bond points comprising less than about 30% of the surface area of said laminate.

28. The breathable barrier laminate of claim 4 wherein said breathable fibrous layer comprises a nonwoven web and wherein said nonwoven web is point bonded and further wherein the bond points comprise less than about 30% of the surface area of said laminate.

29. The breathable barrier laminate of claim 7 wherein said laminate has a WVTR in excess of 1500 g/m$^2$/day.

30. The breathable barrier laminate of claim 29 wherein the base film and intermediate film have a combined basis weight of between about 15 g/m$^2$ and about 35 g/m$^2$.

* * * * *